United States Patent
Wagner

(10) Patent No.: US 9,737,758 B1
(45) Date of Patent: *Aug. 22, 2017

(54) METHOD AND SYSTEM FOR GENERATING ATHLETIC SIGNATURES

(71) Applicant: SPARTA SOFTWARE CORPORATION, Menlo Park, CA (US)

(72) Inventor: Phillip Patrick Wagner, Menlo Park, CA (US)

(73) Assignee: SPARTA SOFTWARE CORPORATION, Menlo Park, CA (US)

(*) Notice: Subject to any disclaimer, the term of this patent is extended or adjusted under 35 U.S.C. 154(b) by 236 days.

This patent is subject to a terminal disclaimer.

(21) Appl. No.: 14/033,279

(22) Filed: Sep. 20, 2013

(51) Int. Cl.
*A63B 24/00* (2006.01)

(52) U.S. Cl.
CPC ................ *A63B 24/0062* (2013.01)

(58) Field of Classification Search
CPC .............. A63B 24/0062; A63B 71/06; A63B 2220/803; A63B 24/0021; A63B 69/0028; A63B 2024/0065; A63B 24/003; A63B 5/00; A63B 2024/0009; A61B 5/11; A61B 2503/10; G06T 7/20

See application file for complete search history.

(56) References Cited

U.S. PATENT DOCUMENTS

| 6,539,327 | B1* | 3/2003 | Dassot | G01V 3/081 |
| | | | | 702/150 |
| 6,786,730 | B2* | 9/2004 | Bleckley | A63B 24/0003 |
| | | | | 434/247 |
| 7,670,263 | B2* | 3/2010 | Ellis | A61B 5/1038 |
| | | | | 342/357.75 |
| 8,858,400 | B2* | 10/2014 | Johnson | A63B 24/0075 |
| | | | | 482/1 |

(Continued)

OTHER PUBLICATIONS

"Coaches' Guide to Sports Injuries," Randolph Hospital, Dec. 18, 2010.*

(Continued)

*Primary Examiner* — David L Lewis
*Assistant Examiner* — Matthew D. Hoel
(74) *Attorney, Agent, or Firm* — One LLP

(57) ABSTRACT

A method for profiling an athlete is discloses. The method comprises storing force-time data for a population of athletes; wherein said force-time data is generated by a sensor system in respect of each of said plurality of athletes in response to the said athlete performing an athletic movement, and comprises values for a concentric net vertical impulse (CON-IMP), an average eccentric rate of force development (ECC-RFD), and an average vertical concentric force (CON-VF); performing a normalization of the force-time data for each athlete based on values of the force-time data within the population of athletes; and generating a profile comprising an athletic signature for each athlete in the population, wherein said profile comprises the (Continued)

normalized values for the concentric net vertical impulse (CON-IMP), the average eccentric rate of force development (ECC-RFD), and the average vertical concentric force (CON-VF) for the athlete.

20 Claims, 4 Drawing Sheets

(56) References Cited

U.S. PATENT DOCUMENTS

| | | | | |
|---|---|---|---|---|
| 2009/0030350 A1* | 1/2009 | Yang | A61B 5/1038 | 600/595 |
| 2009/0062627 A1* | 3/2009 | Younger | A63B 24/0003 | 600/301 |
| 2009/0069722 A1* | 3/2009 | Flaction | G06K 9/00342 | 600/587 |
| 2009/0210078 A1* | 8/2009 | Crowley | G06Q 30/02 | 700/91 |
| 2010/0173732 A1* | 7/2010 | Vaniche | A63B 24/0003 | 473/422 |
| 2010/0317489 A1* | 12/2010 | Flaction | A61B 5/11 | 482/9 |
| 2012/0023163 A1* | 1/2012 | Mangold | A63B 69/00 | 709/203 |
| 2012/0029666 A1* | 2/2012 | Crowley | A63B 24/0062 | 700/91 |
| 2012/0071733 A1* | 3/2012 | Grey | G06F 19/3481 | 600/301 |
| 2012/0212505 A1* | 8/2012 | Burroughs | G09B 19/0038 | 345/629 |
| 2013/0079907 A1* | 3/2013 | Homsi | A63B 24/00 | 700/91 |
| 2013/0252216 A1* | 9/2013 | Clavin | G09B 19/0038 | 434/257 |
| 2014/0074179 A1* | 3/2014 | Heldman | A61B 5/1101 | 607/45 |
| 2014/0074265 A1* | 3/2014 | Arginsky | A63B 71/0622 | 700/91 |
| 2014/0180173 A1* | 6/2014 | Sullivan | A61B 5/112 | 600/595 |
| 2014/0287391 A1* | 9/2014 | Krull | A63B 69/00 | 434/247 |
| 2014/0336796 A1* | 11/2014 | Agnew | A43B 3/0005 | 700/91 |
| 2015/0154403 A1* | 6/2015 | Dornbush | A63B 71/06 | 700/91 |

OTHER PUBLICATIONS

"Clinical Practice Guide for Muscular Injuries. Epidemiology, Diagnosis, Treatment and Prevention," Medical Services, Futbol Club Barcelona, Feb. 9, 2009.*

"Net Impulse and Net Impulse Characteristics in Vertical Jumping," Satoshi Mizuguchi, 2012.*

* cited by examiner

US 9,737,758 B1

METHOD AND SYSTEM FOR GENERATING ATHLETIC SIGNATURES

FIELD

Embodiments of the present invention relate to athletic performance. In particular, embodiments of the present invention relate to systems for analyzing athletic movement

BACKGROUND

Sensors may be used to capture data for athletes during performance of an athletic movement. For example, a sensor may comprise a force-plate and the athletic movement may comprise a vertical jump initiated while standing on the force-plate in a static position.

However, the inventor has found that there is not a systematic way to analyze that data from the sensors in a manner that improves athletic performance.

SUMMARY

According to a first aspect of the invention, there is provided a method for profiling an athlete, the method comprising:

storing force-time data for a population of athletes; wherein said force-time data is generated by a sensor system in respect of each of said plurality of athletes in response to the said athlete performing an athletic movement, and wherein said force-time data comprises values for a concentric net vertical impulse (CON-IMP), an average eccentric rate of force development (ECC-RFD), and an average vertical concentric force (CON-VF);

performing a normalization of the force-time data for each athlete based on values of the force-time data within the population of athletes; and generating a profile comprising an athletic signature for each athlete in the population, wherein said profile comprises the normalized values for the concentric net vertical impulse (CON-IMP), the average eccentric rate of force development (ECC-RFD), and the average vertical concentric force (CON-VF) for the athlete.

Other aspects of the invention will be apparent from the detailed description below.

DETAILED DESCRIPTION

In the following description, for purposes of explanation, numerous specific details are set forth in order to provide a thorough understanding of the invention. It will be apparent, however, to one skilled in the art that the invention can be practiced without these specific details. In other instances, structures and devices are shown in block or flow diagram form only in order to avoid obscuring the invention.

Reference in this specification to "one embodiment" or "an embodiment" means that a particular feature, structure, or characteristic described in connection with the embodiment is included in at least one embodiment of the invention. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Moreover, although the following description contains many specifics for the purposes of illustration, anyone skilled in the art will appreciate that many variations and/or alterations to the details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Figure 1:
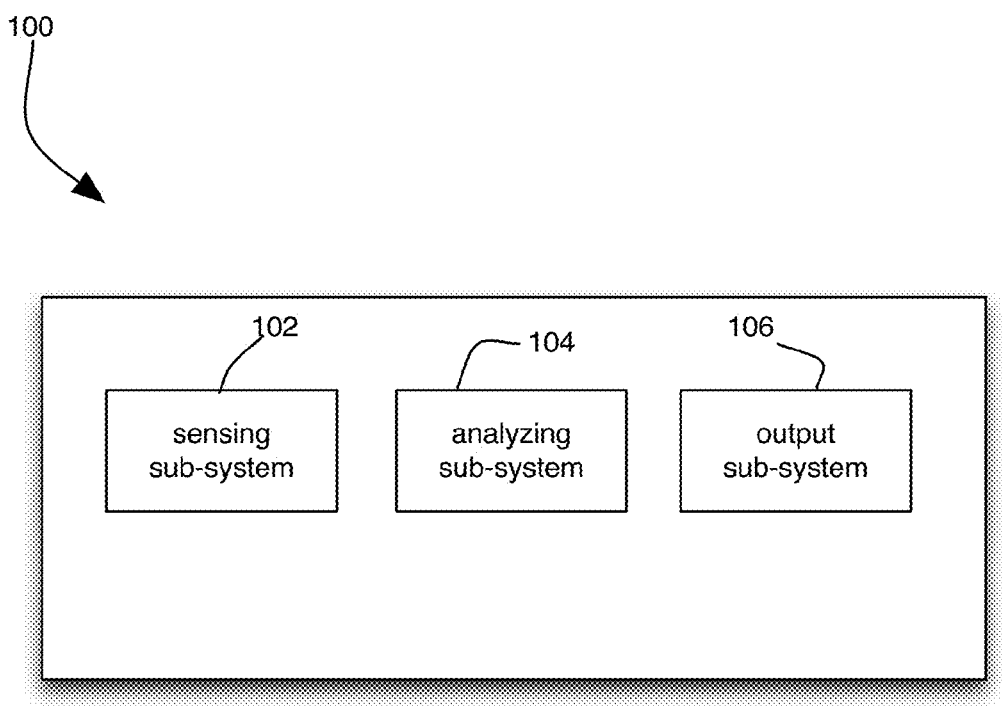
FIG. 1 shows a logical block diagram of a system to analyze athletic movement, in accordance with one embodiment of the invention.

Referring to FIG. 1, embodiments of the present invention disclose a system 100 for analyzing athletic movement. For illustrative purposes consider the athletic movement to be a vertical jump. However, it is to be understood that the system may be used to analyze other forms of athletic movement, such as golf and baseball swings, baseball and football throws, sprinting, agility, basketball shooting, and kicking.

The system 100 may, at least logically, be divided into a sensing sub-system 102, an analytical sub-system 104, and an output sub-system 106.

Figure 2:
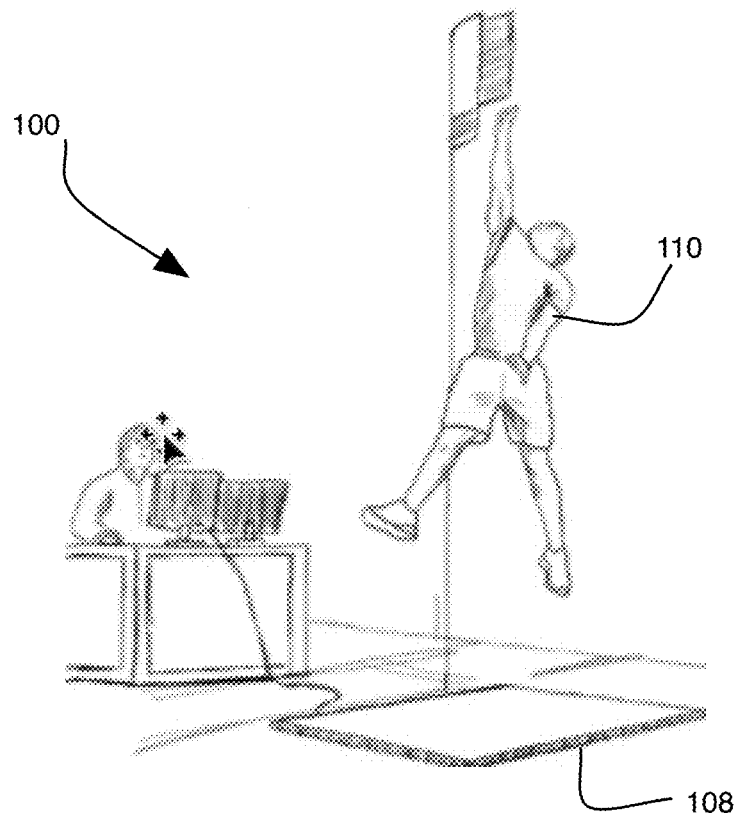
FIG. 2 shows the system of FIG. 1 implemented with a force-plate, in accordance with one embodiment of the invention

The sensing sub-system 102 may include sensors for sensing a time-dependent variable that changes during the athletic movement. In one embodiment, the sensing sub-system 102 may include a sensor in the form of a force-plate 108, as shown in FIG. 2. In other embodiments, the sensing sub-system 102 may include other types of sensors. For example, in one embodiment, the sensing sub-system 102 may include an accelerometer, which may be integrated, for example, into a bracelet or a shoe pod. In use, an athlete 110 initiates a vertical jump (athletic movement) on the force plate 108. The force plate records changes in force over time (typically one force reading is captured each millisecond). An analog-to-digital converter (not shown) converts the analog force signal into a digital signal for analysis by the analytical sub-system 104.

The analytical sub-system 104 may include instructions to process the digital signal in order to compile an athletic signature for the athlete 110. In one embodiment, the analytical sub-system 104 extracts selected portions of a force-time curve output by the sensing sub-system 102. Said selected portions may comprise phases of the jump including a load phase, an explode phase, and a drive phase, as detailed below:

(a) load phase: comprises data relating to the average eccentric rate of force development during the jump.

(b) explode phase: comprises data relating to the average relative concentric peak force generated during the jump, computed as average concentric peak force divided by the athlete's weight.

(c) drive phase: comprises data relating to the concentric relative impulse for the jump.

Typically, the system 100 is configured to process a plurality of jumps for each athlete and to store data for each athlete in the form of an athletic signature Each athletic signature may be used to profile an athlete in terms of at least one of: suitability for a given sport, proneness to injury, suitability for particular athletic gear (e.g. shoes), etc., as will now be described.

Figure 3:
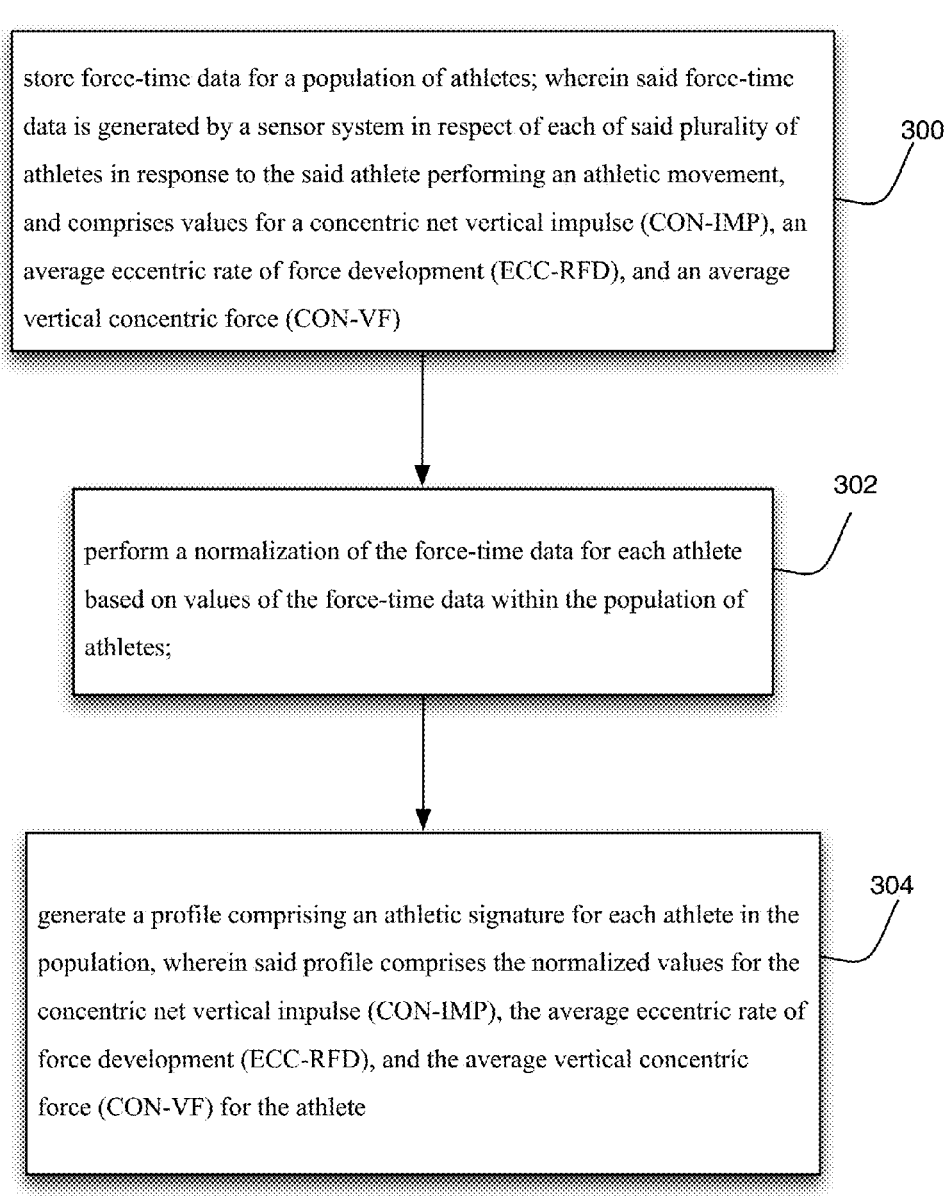
FIG. 3 shows a flowchart of a method for generating signatures for athletes, in accordance with one embodiment of the invention.

FIG. 3 shows a flowchart corresponding to a method for generating a signature for an athlete, in accordance with one embodiment. The method includes the following processing blocks:

Block 300: in this block force-time data for a population of athletes is stored in memory. Said force-time data may be generated by a sensing sub-system 102 in respect of each of said plurality of athletes in response to the said athlete performing an athletic movement, and comprises values for a concentric net vertical impulse (CON-IMP), an average eccentric rate of force development (ECC-RFD), and an average vertical concentric force (CON-VF);

Block 302: in this block a normalization of the force-time data for each athlete based on values of the force-time data within the population of athletes is performed;

Block 304: in this block a profile comprising an athletic signature is generated for each athlete in the population, wherein said profile comprises the normalized values for the concentric net vertical impulse (CON-IMP), the average eccentric rate of force development (ECC-RFD), and the average vertical concentric force (CON-VF) for the athlete.

In one embodiment, performing the normalization comprises calculating a T-score for concentric net vertical impulse (CON-IMP), average eccentric rate of force development (ECC-RFD), and average vertical concentric force (CON-VF) for each athlete. Each T-score may be calculated as an average over a standard deviation.

In one embodiment, the population of athletes may comprise athletes who play a particular sport.

In one embodiment, the population of athletes may comprise athletes who play a particular position within a particular sport.

The method may further comprise analyzing the athletic signatures of elite athletes and characterizing said signatures into an archetypal signature corresponding to one of a role within a sport and a sport.

In one embodiment, the force-time data comprises repeating data collected for each athlete when performing the same athletic movement at different times.

The output sub-system 106 facilitates output of athletic signatures via printout, display, etc.

Figure 4:
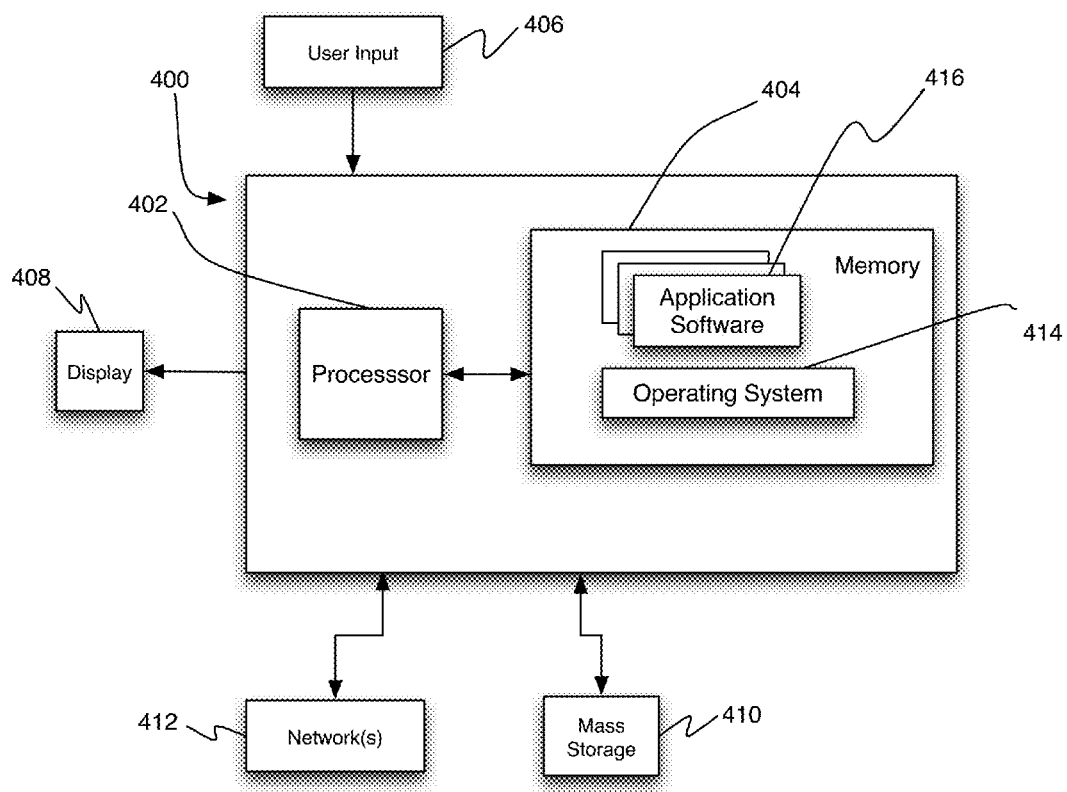
FIG. 4 shows a high-level block diagram of hardware used to implement the system of FIG. 1, in accordance with one embodiment of the invention.

FIG. 4 shows an example of hardware 400 that may be used to implement portions of the system 100, in accordance with one embodiment. The hardware 400 may include at least one processor 402 coupled to a memory 404. The processor 402 may represent one or more processors (e.g., microprocessors), and the memory 404 may represent random access memory (RAM) devices comprising a main storage of the hardware, as well as any supplemental levels of memory e.g., cache memories, non-volatile or back-up memories (e.g. programmable or flash memories), read-only memories, etc. In addition, the memory 404 may be considered to include memory storage physically located elsewhere in the hardware, e.g. any cache memory in the processor 402, as well as any storage capacity used as a virtual memory, e.g., as stored on a mass storage device.

The hardware 400 also typically receives a number of inputs and outputs for communicating information externally. For interface with a user or operator, the hardware 400 may include one or more user input/output devices 406 (e.g., force-plate, keyboard, mouse, etc.) and a display 408. For additional storage, the hardware 400 may also include one or more mass storage devices 410, e.g., a Universal Serial Bus (USB) or other removable disk drive, a hard disk drive, a Direct Access Storage Device (DASD), an optical drive (e.g. a Compact Disk (CD) drive, a Digital Versatile Disk (DVD) drive, etc.) and/or a USB drive, among others. Furthermore, the hardware 400 may include an interface with one or more networks 412 (e.g., a local area network (LAN), a wide area network (WAN), a wireless network, and/or the Internet among others) to permit the communication of information with other computers coupled to the networks. It should be appreciated that the hardware 400 typically includes suitable analog and/or digital interfaces between the processor 402 and each of the components, as is well known in the art.

The hardware 400 operates under the control of an operating system 414, and executes application software 416 which includes various computer software applications, components, programs, objects, modules, etc. to perform the techniques described above.

In general, the routines executed to implement the embodiments of the invention, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, USB and other removable media, hard disk drives, optical disks (e.g., Compact Disk Read-Only Memory (CD ROMS), Digital Versatile Disks, (DVDs), etc.), flash drives among others.

Although the present invention has been described with reference to specific exemplary embodiments, it will be evident that the various modification and changes can be made to these embodiments without departing from the broader spirit of the invention. Accordingly, the specification and drawings are to be regarded in an illustrative sense rather than in a restrictive sense.

The invention claimed is:

1. A method for profiling an athlete, the method comprising:
  receiving a plurality of analog signals, by a sensing sub-system, wherein the plurality of analog signals comprises force-time data correlating to a vertical jump performed by each athlete within a population of athletes;
  converting, by an analog-to-digital converter, each of the plurality of analog signals into a digital signal;
  extracting, by an analytical sub-system, selected portions of the force-time data, the selected portions comprising: a load phase measurement comprising an average eccentric rate of force development during the vertical jump, an explode phase measurement comprising an average relative concentric force during the vertical jump divided by a weight of the athlete, and a drive phase measurement comprising a concentric relative impulse during the vertical jump;

performing a normalization of the force-time data for each athlete based on values of the force-time data within the population of athletes;

storing the selected portions associated with each athlete to a mass storage device as an athletic signature; and generating a profile for each athlete based on the athletic signature, wherein the profile is in terms of at least one of suitability for a given sport, proneness to injury, and suitability for particular athletic gear.

2. The method of claim 1, wherein performing the normalization comprises calculating a T-score, for each athlete, for the drive phase measurement comprising the concentric relative impulse during the vertical jump, the load phase measurement comprising the average eccentric rate of force development during the vertical jump, and the explode phase measurement comprising the average relative concentric force during the vertical jump divided by the weight of the athlete.

3. The method of claim 2, wherein each T-score is calculated as an average over a standard deviation.

4. The method of claim 1, wherein the population of athletes comprises athletes who play a particular sport.

5. The method of claim 1, wherein the population of athletes comprises athletes who play a particular position within a particular sport.

6. The method of claim 1, further comprising analyzing the athletic signatures of elite athletes and characterizing said signatures into an archetypal signature corresponding to one of a role within a sport and a sport.

7. The method of claim 1, wherein the force-time data comprises repeating data collected for each athlete when performing the vertical jump at different times.

8. The method of claim 1, wherein the vertical jump comprises a vertical jump from a static position, and the sensing sub-system comprises a force plate.

9. A non-transitory computer-readable medium comprising instructions which when executed by a processing system causes said system to perform a method for profiling an athlete, the method comprising:

receiving a plurality of analog signals by a sensing sub-system, wherein the plurality of analog signals comprises force-time data correlating to a vertical jump performed by each athlete within a population of athletes;

converting, by an analog-to-digital converter, each of the plurality of analog signals into a digital signal;

extracting, by an analytical sub-system, selected portions of the force-time data, the selected portions comprising: a load phase measurement comprising an average eccentric rate of force development during the vertical jump, an explode phase measurement comprising an average relative concentric force during the vertical jump divided by a weight of the athlete, and a drive phase measurement comprising a concentric relative impulse during the vertical jump;

performing a normalization of the force-time data for each athlete based on values of the force-time data within the population of athletes;

storing the selected portions associated with each athlete to a mass storage device as an athletic signature; and generating a profile for each athlete based on the athletic signature, wherein the profile is in terms of at least one of suitability for a given sport, proneness to injury, and suitability for particular athletic gear.

10. The computer-readable medium of claim 9, wherein performing the normalization comprises calculating a T-score, for each athlete, for the drive phase measurement comprising the concentric relative impulse during the vertical jump, the load phase measurement comprising the average eccentric rate of force development during the vertical jump, and the explode phase measurement comprising the average relative concentric force during the vertical jump divided by the weight of the athlete.

11. The computer-readable medium of claim 9, wherein each T-score is calculated as an average over a standard deviation.

12. The computer-readable medium of claim 9, wherein the population of athletes comprises athletes who play a particular sport.

13. A system, comprising:

a processor; and a memory coupled to the processor, the memory storing instructions which when executed by the processor, cause the processor to perform a method for profiling an athlete, the method comprising:

receiving a plurality of analog signals by a sensing sub-system, wherein the plurality of analog signals comprises force-time data correlating to a vertical jump performed by each athlete within a population of athletes;

converting, by an analog-to-digital converter, each of the plurality of analog signals into a digital signal;

extracting, by an analytical sub-system, selected portions of the force-time data, the selected portions comprising: a load phase measurement comprising an average eccentric rate of force development during the vertical jump, an explode phase measurement comprising an average relative concentric force during the vertical jump divided by a weight of the athlete, and a drive phase measurement comprising a concentric relative impulse during the vertical jump;

performing a normalization of the force-time data for each athlete based on values of the force-time data within the population of athletes;

storing the selected portions associated with each athlete to a mass storage device as an athletic signature; and generating a profile for each athlete based on the athletic signature, wherein the profile is in terms of at least one of suitability for a given sport, proneness to injury, and suitability for particular athletic gear.

14. The system of claim 13, wherein performing the normalization comprises calculating a T-score, for each athlete, for the drive phase measurement comprising the concentric relative impulse during the vertical jump, the load phase measurement comprising the average eccentric rate of force development during the vertical jump, and the explode phase measurement comprising the average relative concentric force during the vertical jump divided by the weight of the athlete.

15. The system of claim 14, wherein each T-score is calculated as an average over a standard deviation.

16. The system of claim 13, wherein the population of athletes comprises athletes who play a particular sport.

17. The system of claim 13, wherein the population of athletes comprises athletes who play a particular position within a particular sport.

18. The system of claim 13, wherein the method further comprises analyzing the athletic signatures of elite athletes and characterizing said signatures into an archetypal signature corresponding to one of a role within a sport and a sport.

19. The system of claim 13, wherein the force-time data comprises repeating data collected for each athlete when performing the vertical jump at different times.

20. The system of claim 13, wherein the vertical jump comprises a vertical jump from a static position, and the sensing sub-system comprises a force plate.

* * * * *